United States Patent
Augustine et al.

(10) Patent No.: US 8,986,359 B2
(45) Date of Patent: Mar. 24, 2015

(54) MULTI-ZONE ELECTRIC WARMING BLANKET

(75) Inventors: Scott D. Augustine, Bloomington, MN (US); Ryan S. Augustine, Minneapolis, MN (US); Randall C. Arnold, Minnetonka, MN (US); Keith J. Leland, Medina, MN (US); Joshua P. Waldman, Edina, MN (US); Rudolf A. Deibel, Eden Prairie, MN (US); Thomas F. Neils, Minneapolis, MN (US)

(73) Assignee: Augustine Temperature Management LLC, Eden Prairie, MN (US)

( * ) Notice: Subject to any disclaimer, the term of this patent is extended or adjusted under 35 U.S.C. 154(b) by 1025 days.

(21) Appl. No.: 12/249,896

(22) Filed: Oct. 10, 2008

(65) Prior Publication Data

US 2009/0099631 A1    Apr. 16, 2009

Related U.S. Application Data

(60) Provisional application No. 60/979,678, filed on Oct. 12, 2007.

(51) Int. Cl.
| | | |
|---|---|---|
| *A61F 7/00* | (2006.01) | |
| *A61F 7/12* | (2006.01) | |
| *H05B 1/00* | (2006.01) | |
| *H05B 3/00* | (2006.01) | |
| *H05B 11/00* | (2006.01) | |
| *H05B 3/06* | (2006.01) | |
| *H05B 3/34* | (2006.01) | |
| *A61F 7/02* | (2006.01) | |

(52) U.S. Cl.
CPC ............... *H05B 3/342* (2013.01); *A61F 7/007* (2013.01); *A61F 2007/0029* (2013.01); *A61F 2007/0228* (2013.01); *A61F 2007/0288* (2013.01); *H05B 2203/011* (2013.01); *H05B 2203/017* (2013.01)
USPC .............. 607/96; 607/108; 219/212; 219/527

(58) Field of Classification Search
USPC ............. 607/96, 108–111; 219/212, 527–529
See application file for complete search history.

(56) References Cited

U.S. PATENT DOCUMENTS

| | | | |
|---|---|---|---|
| 3,634,655 A | 1/1972 | Jordan | |
| 4,930,317 A * | 6/1990 | Klein | ................................ 62/3.3 |
| 6,348,678 B1 * | 2/2002 | Loyd et al. | .................... 219/530 |
| 2002/0047007 A1 * | 4/2002 | Loyd et al. | .................... 219/530 |
| 2006/0191675 A1 * | 8/2006 | Fletcher et al. | ............... 165/172 |
| 2007/0101996 A1 * | 5/2007 | Carstens | .................. 128/206.12 |
| 2007/0106353 A1 * | 5/2007 | Carstens | ....................... 607/112 |
| 2007/0106355 A1 * | 5/2007 | Carstens | ....................... 607/112 |

FOREIGN PATENT DOCUMENTS

WO    2007041389 A1    4/2004

OTHER PUBLICATIONS

PCT/US2008/079662, International Search Report and Written Opinion, dated Jan. 28, 2009, 14 pages.

* cited by examiner

*Primary Examiner* — Nathan R Price
(74) *Attorney, Agent, or Firm* — Fredrikson & Byron, P.A.

(57) ABSTRACT

A multi-zone electric heating blanket. The blanket may be shaped to cover the outstretched arms or other body parts of a patient. The blanket includes first and second body part portions and a connecting bridge. The interconnection via the bridge leaves an open gap between the first and second body part portions for unblocked access to the patient. A power controller may supply power to heating elements in both body part portions based on a temperature sensor in one of the body part portions.

23 Claims, 8 Drawing Sheets

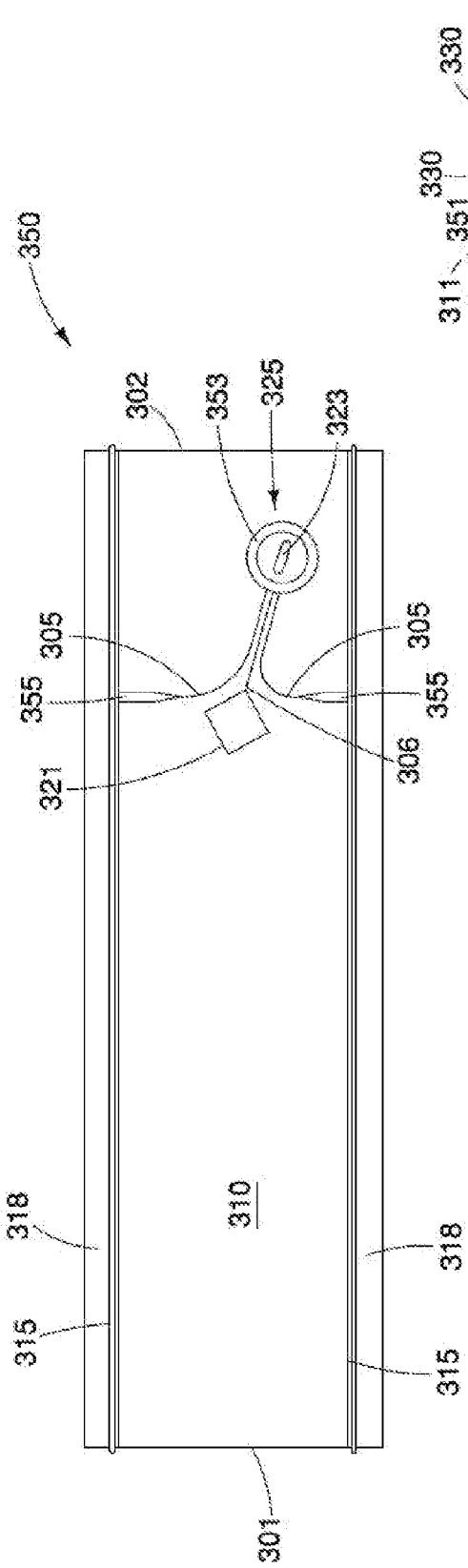
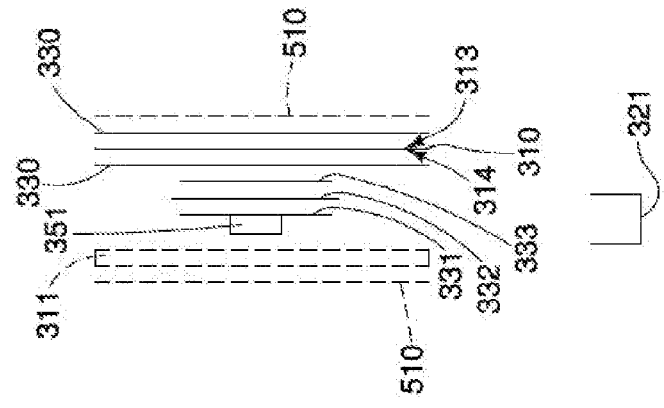
FIG. 4A
FIG. 4B

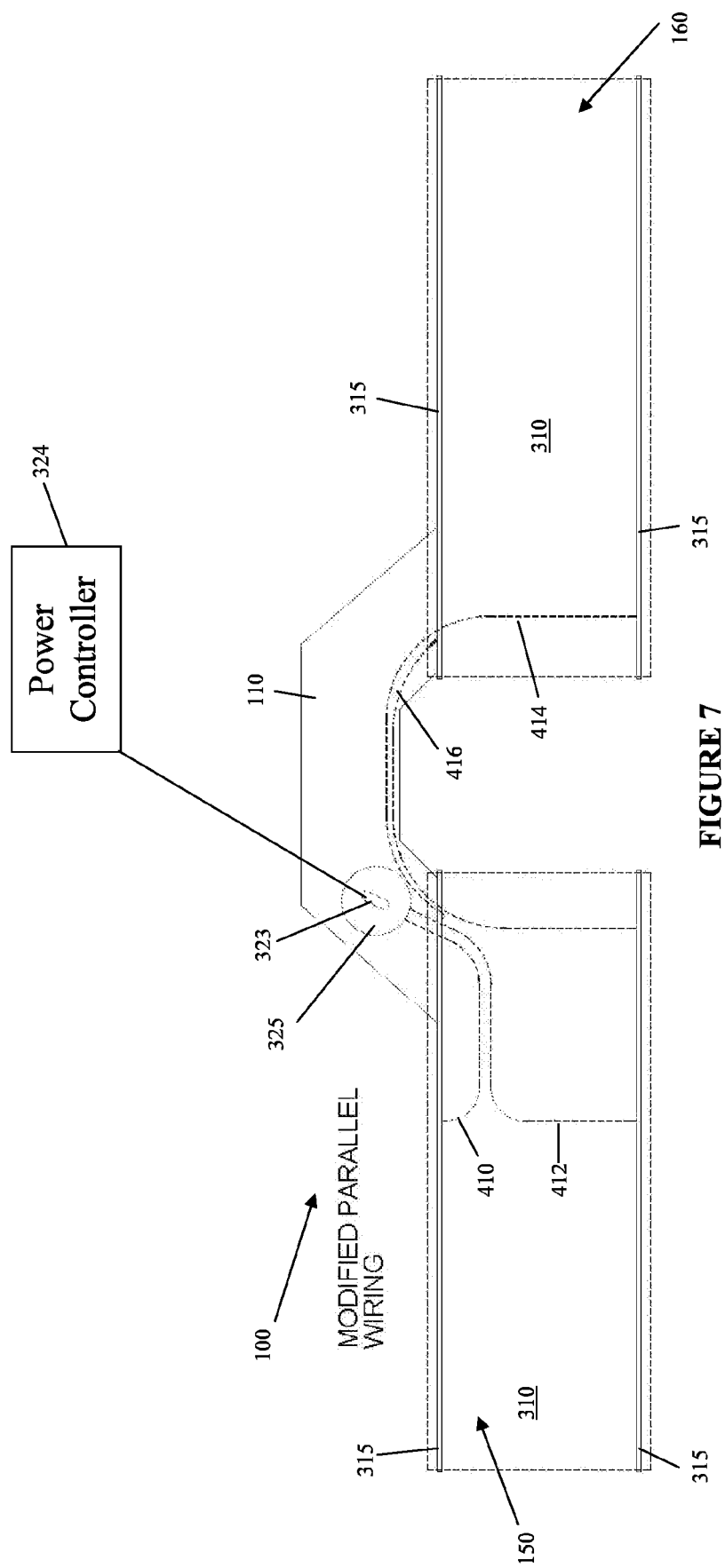

MULTI-ZONE ELECTRIC WARMING BLANKET

PRIORITY CLAIM

The present application claims priority to provisional application Ser. No. 60/979,678, entitled MULTI-ZONE ELECTRIC WARMING BLANKET FOR UPPER BODY PATIENT WARMING filed on Oct. 12, 2007; the specification of which is incorporated by reference in its entirety herein.

TECHNICAL FIELD

The present invention is related to heating or warming blankets or pads and more particularly to those including electrical heating elements.

BACKGROUND

It is well established that surgical patients under anesthesia become poikilothermic. This means that the patients lose their ability to control their body temperature and will take on or lose heat depending on the temperature of the environment. Since modern operating rooms are all air conditioned to a relatively low temperature for surgeon comfort, the majority of patients undergoing general anesthesia will lose heat and become clinically hypothermic if not warmed.

Over the past 15 years, forced-air warming (FAW) has become the "standard of care" for preventing and treating the hypothermia caused by anesthesia and surgery. FAW consists of a large heater/blower attached by a hose to an inflatable air blanket. The warm air is distributed over the patient within the chambers of the blanket and then is exhausted onto the patient through holes in the bottom surface of the blanket.

Although FAW is clinically effective, it suffers from several problems including: a relatively high price; air blowing in the operating room, which can be noisy and can potentially contaminate the surgical field; and bulkiness, which, at times, may obscure the view of the surgeon. Moreover, the low specific heat of air and the rapid loss of heat from air require that the temperature of the air, as it leaves the hose, be dangerously high—in some products as high as 45° C. This poses significant dangers for the patient. Second and third degree burns have occurred both because of contact between the hose and the patient's skin, and by blowing hot air directly from the hose onto the skin without connecting a blanket to the hose. This condition is common enough to have its own name—"hosing." The manufacturers of forced air warming equipment actively warn their users against hosing and the risks it poses to the patient.

To overcome the aforementioned problems with FAW, several companies have developed electric warming blankets. However, these electric blankets have a number of inadequacies, for example, the risk of heat and pressure injuries that may be suffered by a patient improperly coming into contact with the electrical heating elements of these blankets. It is well established that heat and pressure applied to the skin can rapidly cause thermal injury to that skin. Such contact may arise if a patient inadvertently lies on an edge of a heated blanket, if a clinician improperly positions an anesthetized patient atop a portion of the heated blanket, or if a clinician tucks a heated edge of the blanket about the patient. Thus, there is a need for a heating blanket that effectively forms a cocoon about a patient, in order to provide maximum efficacy in heating, without posing the risk of burning the patient.

There is also a need for electrically heated blankets or pads that can be used safely and effectively to warm patients undergoing surgery or other medical treatments. These blankets need to be flexible in order to effectively drape over the patient (making excellent contact for conductive heat transfer and maximizing the area of the patient's skin receiving conductive as well as radiant heat transfer), and should incorporate means for precise temperature control.

Electric blankets are used to maintain a patient's body temperature in a wide variety of surgical procedures. The sterile surgical field in each procedure can be quite different, and electric blankets of varying sizes and shapes are needed in order to cover a maximum amount of body surface area surface outside the surgical field. For example, a blanket that only covers a lower abdomen and legs of a patient can be used during upper body surgeries. Similarly, a blanket that covers outstretched arms and a chest area of a patient is useful for patients undergoing lower body surgery.

Upper body warming blankets that drape across the arms and chest are useful but block access to the chest. Such access may be needed, such as for surgical site preparation or for access to EKG leads on the chest during surgery. In addition, the chest portion of such blankets can also rub against the patient's neck and chin, potentially causing patient discomfort. Furthermore, such blankets require that the patient's arms be extended at a 90 degree angle from the patient's body. This position may not always be preferred and the lack of adjustability or alternative positions may lead to discomfort for some patients. The maximum width of the heated portion of a standard warming blanket is also limited by the available space between the patients chin/neck and the upper edge of the surgical prep site and drapes. In small patients, or in cases where the surgical prep site extends up to or past the nipple line, the blanket must be very narrow, or it may end up extending up and over the patients face which is undesirable.

It may also be desirable that such upper body blankets be adaptable for placement over other body parts, such as the legs of the patients.

Accordingly, there remains a need for flexible heater sub-assemblies and blankets that effectively cover a desired amount of body surface in a variety of arm positions without rubbing against the chin or neck and without blocking access to the chest. Various embodiments of the invention described herein solve one or more of the problems discussed above.

SUMMARY

Certain embodiments of the present invention relate to a multi-zone heating blanket. In some embodiments, the blanket includes a first body part portion, a second body part portion, and an interconnecting bridge. The first body part portion may contain a first heating element or heating element assembly adapted for placement over a first body part of the patient, and the second body part portion may contain a second heating element or heating element assembly adapted for placement over a second body part of the patient. In some embodiments, the bridge portion interconnects the first and second body part portions at or near proximal ends thereof in a manner to leave an open gap between such proximal ends. In other embodiments, the bridge portion includes electrical wiring connecting the first and second heating elements The open gap provides unblocked access to the portion of the patient positioned between the two body part portions.

In some embodiments, the first and second body parts are first and second arms of the patient. In these embodiments, the multi-zone heating blanket is shaped to cover the outstretched arms of the patient and the open gap leaves the patient's chest unblocked and accessible. The bridge may be placed underneath the patient's head in such embodiments.

In other embodiments, the first and second body parts are first and second legs of the patient. The bridge in such embodiments may placed over the patient's abdomen and the open gap leaves the patient's groin area unblocked and accessible.

In some embodiments, the multi-zone heating blanket includes a first body part portion, a second body part portion, a bridge portion, a temperature sensor, and a power controller. The first and second body part portions contain respective first and second heating element assemblies electrically interconnected via the bridge. Each heating element assembly contains two bus bars electrically connected via respective conductive sheets that have approximately equal watt density outputs when powered. The temperature sensor is coupled to one of the conductive sheets at a location likely to be in heat conductive contact with the patient. The power controller supplies power to first and second heating element assemblies based on the temperature sensed by the temperature sensor.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 4A is a top plan view of a heating element assembly, according to some embodiments of the present invention, which may be incorporated in the blanket shown in FIG. 1A or 1B;

FIG. 4B is a section view through section line A-A of FIG. 4A;

FIG. 7 is a schematic view of a multi-zone heating blanket, according to some embodiments of the present invention, showing parallel wiring.

DETAILED DESCRIPTION

Figure 1A:
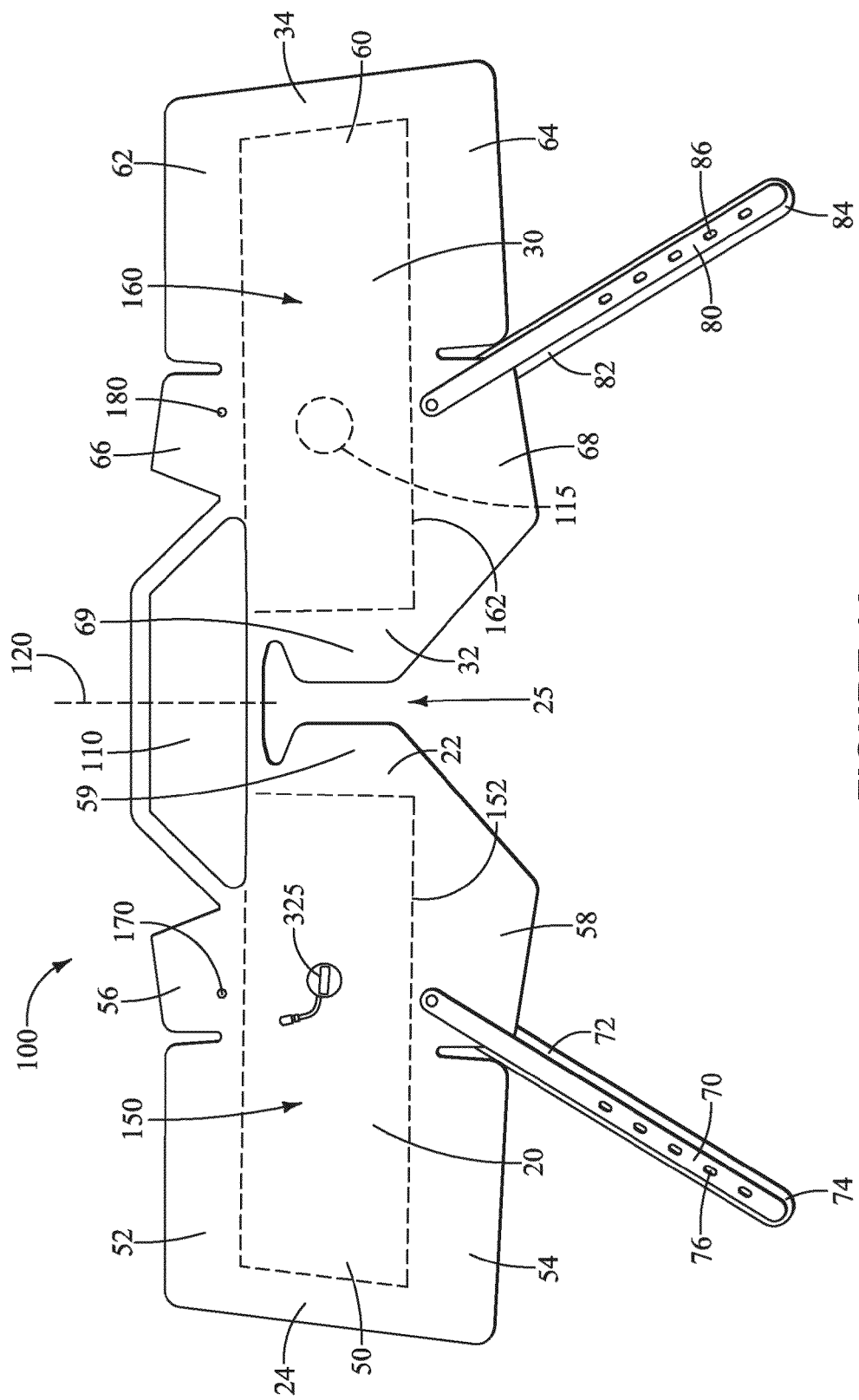
FIG. 1A is a top plan view of a multi-zone heating blanket, according to some embodiments of the present invention.

The following discussion is presented to enable a person skilled in the art to make and use the invention. Various modifications to the illustrated embodiments will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the invention. Skilled artisans will recognize the examples provided herein have many useful alternatives which fall within the scope of the invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized. The term 'blanket', used to describe embodiments of the present invention, may be considered to encompass heating blankets and pads.

FIG. 1A is a top plan view of a multi-zone heating blanket 100, according to some embodiments of the present invention, which may be used to keep a patient warm during surgery. FIG. 1A illustrates blanket 100 having a first body part portion 20 having a proximal end 22 and a distal end 24, a second body part portion 30 having a proximal end 32 and a distal end 34, and a bridge portion 110. The bridge portion 110 is attached at or near the proximal ends 22, 32 of the first and second body part portions 20, 30 and connects the two body part portions 20, 30. In the embodiment shown in FIG. 1A, the body part portions 20, 30 are shaped to be positioned on and cover the patient's arms and may also cover a portion or all of the patient's shoulders. The bridge portion 110 is arcuately shaped to connect the two body part portions 20, 30. In some embodiments and uses, the bridge is positioned behind and beneath the patient's head while the patient rests on the operating table. In this way, the weight of the patient's head helps hold the bridge portion 110 and, correspondingly, the entire blanket 100 in position. Furthermore, because the bridge portion 110 is positioned behind the head, the patient's chest is exposed in an area 25 between the first and second body part portions 20, 30, allowing access to the patient's chest throughout the surgery and without the need to remove the blanket 100. Moreover, the body part portions 20, 30 may be relatively wider than in past designs since the added width will not compromise access to the patient's chest area, as would occur in single zone heating designs that have a single, long heating element strip that stretches across both of the patient's arms. The wider body part portions 20, 30 may provide improved heating yet area 25 remains open and unobstructed. Excluding the flaps, the width of the body part portions 20, 30 may be about 10 to 15 inches. In addition, the bridge portion 110 can provide an area of improved flexibility, so that one of the body part portions 20, 30 can be rotated to accommodate various arm positions yet the other body part portion 30, 20 remains generally flat against the patient's arm.

In alternate embodiments, the bridge portion 110 may be shaped or used in a manner that places it over the patient's chest. In yet another embodiment, the bridge portion 110 may be positioned past the top of the patient's head such that the patient's head rests on a small portion of or none of the bridge portion 110. That is, the placement and size of bridge portion 110 may vary from blanket to blanket depending upon the size of patient, type of surgery, or configuration to be employed.

For instance, in yet another embodiment, the multi-zone blanket 100 is shaped to be placed over the legs of the patient. That is, the first and second body part portions become first and second lower body portions. The bridge portion in such a lower body multi-zone blanket may be positioned over the patient's abdomen in such instances, leaving a gap 25 that provides open and unblocked access to the patient's groin area. In other embodiments, the multi-zone blanket 100 is shaped to be placed over of a patient resting on his or her side. In such a configuration, the first body part may be the exposed (i.e., upper) arm of the patient and the second body part may be exposed (i.e., upper) leg and/or hip of the patient. The flexibility of the bridge portion 110 permits the first and second body part portions to be place in many different locations and configurations on the patient.

The first body part portion 20 includes a first heating element assembly 150 covered by a first flexible shell portion 50. The second body part portion 30 includes a second heating element assembly 160 also covered by a second flexible shell portion 60. The bridge portion is generally non-heated. First heating element assembly 150 is generally rectangular and is outlined by dotted lines 152. Second heating element assembly 160 is also generally rectangular and is outlined by dotted lines 162. Shells 50, 60 protect and isolate assemblies 150, 160 from an external environment of blanket 100 and may further protect a patient disposed beneath blanket 100 from electrical shock hazards. According to preferred embodiments of the present invention, shells 50, 60 are waterproof to prevent fluids, for example, bodily fluids, IV fluids, or cleaning fluids, from contacting assemblies 150, 160, and may further include an anti-microbial element, for example, being a SILVERion™ antimicrobial fabric available from Domestic Fabrics Corporation, or Ultra-Fresh™ from Thomson Research Associates.

According to some embodiments of the present invention, shells 50, 60 include top and bottom sheets extending over either side of assemblies 150, 160; the two sheets of shells 50, 60 are coupled together along a seal zone that extends about a perimeter edge of blanket 100 and within the edge to form various zones, or pockets, where gaps exist between the two sheets. Seal zone creates a perimeter seal for the shells 50, 60 instead of laminating the entire interior surfaces of the shells 50, 60 to assemblies 150, 160. According to an exemplary embodiment of the present invention, shells 50, 60 comprise a PVC film. In an alternate embodiment, shells 50,60 comprise a nylon fabric having an overlay of polyurethane coating to provide waterproofing; the coating is on at least an inner surface of each of the two sheets, further facilitating a heat seal between the two sheets, for example, along the seal zone, according to preferred embodiments. It should be noted that, according to alternate embodiments of the present invention, a covering for heating assemblies, such as heating assemblies 150, 160, may be removable and, thus, include a reversible closure facilitating removal of a heating assembly therefrom and insertion of the same or another heating assembly therein.

FIG. 1A illustrates shell portion 50 forming flaps 52, 54, 56, 58, and 59 and shell portion 60 forming flaps 62, 64, 66, 68, and 69 which mirror each other across the central axis 120. These flaps are unheated and may be tucked under the patient (e.g., the patient's arms when the blanket is positioned over the patient's outstretched arms) or may hang down along the size of the operating table to help trap heat under the blanket. One or more of these flaps may be excluded in alternate embodiments. For instance, flaps 59 and 69 may be removed to increase area 25, allowing, for instance, greater access to the patient's chest when the blanket is positioned over the patient's outstretched arms. Moreover, all of the flaps may be removed in an embodiment intended for use with a disposable cover, as discussed below.

One or more of these flaps may include weighting members which assists the flaps in hanging down and may stiffen the flaps. The weighting members may be held between the sheets of shells 50, 60 surrounding areas of the seal zones. Alternately the flaps can be weighted by attaching weighting members to exterior surfaces thereof. Examples of other suitable weighting members include but are not limited to a metal chain, a metal spring, lead shot, plastic rods and sand. The weighting of the flaps causes them to hang down in order to provide a more secure air seal or cocoon about the patient, so that heat produced by the heating elements is trapped around the body part on which the blanket rests (e.g., around each arm when the blanket is positioned over the patient's outstretched arms). The weighting members may further discourage a clinician from tucking the flaps under the patient as a safety feature to help to prevent a portion of the blanket containing heating element 310 (FIGS. 3A-3B) from coming into relatively high pressure contact with the patient, where it could cause serious burns; as such, the weighting members are relatively stiff and/or form a lump at the outer edge of the flaps. Relatively stiff flap weighting members, for example, batten-like flat plastic slabs, by extending along the length of assemblies 150, 160, may further prevent inadvertent rucking of blanket 100, that is, the folding of blanket 100 over on itself which could lead to over-heating of a portion of heating element 310, as previously described. However, a seal zone extending between weighting members between flaps can predetermine a folding location; the predetermined folding location can prevent overheating (due to the location of sensor assembly 321) or can dictate the placement of super over-temperature sensors (not shown).

Figure 2:
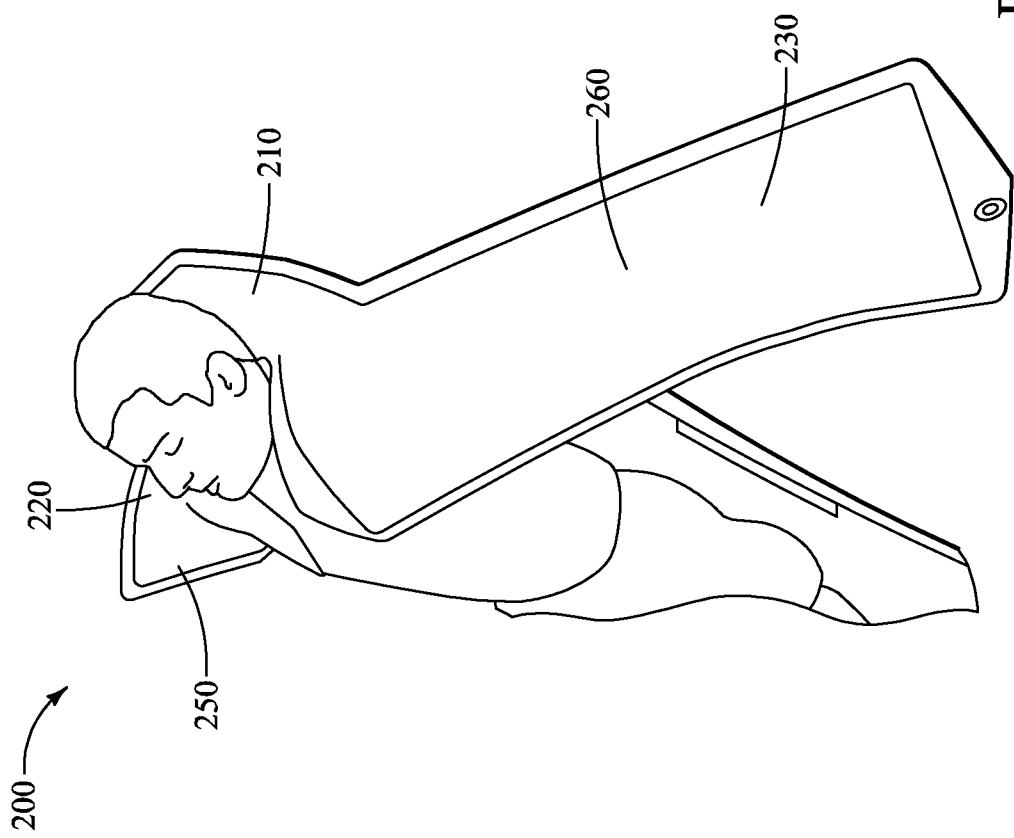
FIG. 2 is a side view of a multi-zone heating blanket draped over an upper body of a patient.

FIG. 2 is a schematic upper end view of an alternative embodiment of a blanket 200 draped over an upper body of a patient. The blanket 200 includes a first body part portion 220 and a second body part portion 230 and a bridge portion 210. In this embodiment, the body part portions are arm portions and the shell portions 250, 260 have straight edges and do not include flaps. Blanket 200 is particularly useful with a disposable cover that keeps the blanket 200 isolated from bodily fluids during use and provides an independent mechanism for affixing the blanket 200 to the patient and/or the underlying operating table.

With further reference to FIG. 1A, it may also be appreciated that, when blanket 100 is positioned over the patient's arms, each strap 70, 80 is positioned in proximity to an elbow of the patient so that either end portion of blanket 100 may be temporarily folded back in order for a clinician to access the patient's arm, for example, to insert or adjust an IV. According to some embodiments of the present invention, super over-temperature sensors are included in blanket 100 being located according to the anticipated folds, for example at general locations 115 illustrated in FIG. 1A, in order to detect over-heating, which may occur if blanket 100 is folded over on itself for too long a time.

In alternative embodiments, the blanket 100 may also include end flaps at the distal ends 24, 34 of the first and second body part portions 20, 30 that include heat seals that form air pockets. FIG. 1A also illustrates first and second straps 70, 80. First strap includes proximal end 72 attached to flap 58 and distal end 74, which can be fastened to flap 56 using notches 76. Likewise proximal end 82 of strap 80 is attached to flap 68 and distal end 84 can be fastened to flap 66 using notches 86.

Multi-zone heating blanket 100 may also include slots (not shown) located on the first and second body part portions 20, 30 of the blanket 100 to act as guides for receiving and holding the straps 70, 80. Slots may be formed in the shells 50, 60 of blanket 100 by many possible techniques. Preferably the slots are cut through a portion of the shells where the top and bottom sheets are coupled together along the seal zone. The slots may be reinforced by sealing a layer of reinforcing material, such as a urethane film or a polyester fiber reinforced PVC, between the layers of the shell around the perimeter of each slot.

Referring back to FIG. 1A, straps 70, 80 may be attached to the front surface of flaps 58, 68 with cooperating fasteners, examples of which include, without limitation, mating hook-and-loop fasteners and/or mating snap fasteners. Alternative embodiments can include straps 70, 80 attaching to the rear surface of flaps 58, 68. In some embodiments, straps 70, 80 can be more permanently attached to flaps 58, 68 with, for example, adhesive, stitching, or a semi-permanent swiveling rivet or snap. In further embodiments, straps 70, 80 can be formed as part of shells 50, 60 and extend out from the edges of flaps 58, 68.

When strapped around the patient's arms, the respective distal ends 74, 84 of first and second straps 70, 80 extend beneath the blanket 100, under operating table arm boards (as described below), and fasten to respective first and second anchor points 170, 180 located on the front surface of blanket 100 via a selected one of the notches 76, 86 that provides an appropriate level of tension on straps 70, 80 to hold blanket 100 in place. In the embodiment shown, anchor points 170, 180 are located proximate to flaps 56, 66 formed by blanket 100. In other embodiments, anchor points 170, 180 may be positioned nearer or farther away from bridge portion 110 or perimeter edge, or may be located on the bottom surface of blanket 100. Anchor points 170, 180 and notches 76, 86 may comprise many different types of connection systems. In one embodiment, anchor points 170, 180 are mushroom-shaped pegs or buttons that extend from the non-heated flap portion of blanket 100. In such embodiments, notches are a series of button holes (e.g., slits) or apertures that may selectively be stretched or deformed to fit over the enlarged top portion of an anchor point and closed underneath the enlarged top portion to remain connected to the anchor point 170, 180.

Straps 70, 80 can then be pulled under the patient's shoulders and/or arms and/or arm boards and fastened to anchor points 170, 180 via appropriate notches 76, 86 on the distal end 74, 84 of straps 70, 80. The perimeter edge of blanket 100, 100' can also be pulled under and back so as to wrap unheated portions of the blanket 100 around the patient's arms. This wrapping action can further decrease heat loss from the patient's arms.

Figure 1B:
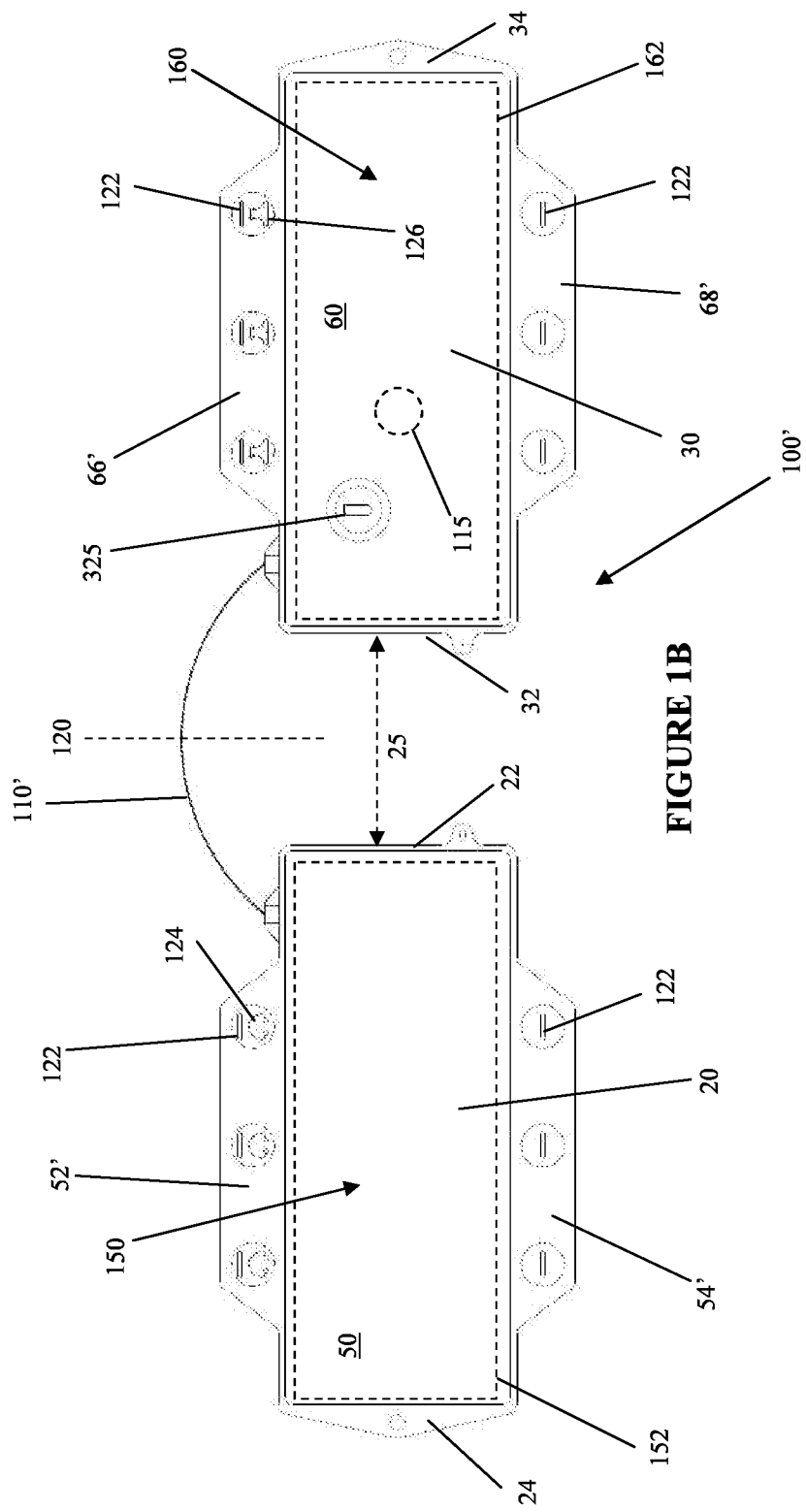
FIG. 1B is a top plan view of a multi-zone heating blanket, according to some alternate embodiments of the present invention.

FIG. 1B is a top plan view of a multi-zone heating blanket 100', according to some alternate embodiments of the present invention. Elements of blanket 100' similar to those in blanket 100 are numbered identically and need not be described separately. In contrast to blanket 100, blanket 100' has a bridge portion 110' that consists essentially of electrical wiring. That is, while bridge portion 110 included electrical wiring that wires the heating assemblies 150, 160 together with plug 325 and any temperature sensors, bridge portion 110' consists essentially of such wiring without also including shell portions 50, 60 that form bridge 110. In this way, bridge portion 110' is narrower and simpler. Bridge portion 110' may be used in the same manners as those described for bridge portion 110, however.

FIG. 1B illustrates shell portion 50 forming flaps 52' and 54', and shell portion 60 forming flap portions 66' and 68', which mirror each other across the central axis 120. Similar to the flaps in FIG. 1A, these flaps are unheated and may be tucked under the patient (e.g., the patient's arm or leg when the blanket is placed over the patient's arms or legs) or may hang down along the side of the operating table to help trap heat under the blanket. One or more of these flaps may be excluded in alternate embodiments. In addition, similar to the flaps in FIG. 1A, one or more of the flaps 52', 54', 66', and 68' in FIG. 1B may include weighting members which assists the flaps in hanging down and may stiffen the flaps.

Multi-zone heating blanket 100' may also include slots located on the first and second body part portions 20, 30 of the blanket 100' to act as guides for receiving and holding straps. In the embodiment shown in FIG. 1B, each of the flaps 52', 54', 66', and 68' includes a row of three slots 122. Slots 122 may be formed in the shells 50, 60 of blanket 100 by many possible techniques. Preferably the slots 122 are cut through a portion of the shells where the top and bottom sheets are coupled together along the seal zone. The slots 122 may be reinforced by sealing a layer of reinforcing material, such as a urethane film or a polyester fiber reinforced PVC, between the layers of the shell around the perimeter of each slot 122.

As noted above, slots 122 may be used with one or more straps to hold the blanket 100' against the patient. For instance, many operating rooms are equipped with straps that have standard hook and loop connectors. A clinician can feed such a strap through opposing slots on the first body part portion or the second body part portion (e.g., one slot 122 on flap 52' to the opposing slot 122 on flap 54'). The strap may be looped around the patient, through the slots 122, and back onto itself for connection to hold blanket 100' in place. For instance, when the blanket 100' is positioned over the patient's arms, the strap can then be pulled under the patient's shoulders and/or arms and/or arm boards and fastened to itself. One or more of the flaps 52', 54', 66', and 68' of blanket 100' can also be pulled under and back so as to wrap unheated portions of the blanket 100' around the patient's arms. This wrapping action can further decrease heat loss from the patient's arms.

In some embodiments, the first body part portion 20 may have a set of connectors that will fasten with a set of connectors on the second body part portion 30. For instance, in the embodiment shown in FIG. 1B, first body part portion 20 contains a row of connectors 124 on flap 52'. Connectors 124 are shaped as an "arrowhead," although other appropriate shapes may be used. Second body part portion 30 contains a row of connectors 126 on flap 66'. Connectors 126 have a modified hourglass shape, although other appropriate shapes may be used in order to mate up with connectors 124. One or more of connectors 124 may be attached to an associated one or more of connectors 126 to allow the first body part portion 20 to be connected to the second body part portion 30 along flaps 52' and 66'. To connect a connector 124 to a connector 126, the arrowhead is inserted into the wider portion of the hourglass and then pulled/slid down into the narrower portion where it is retained. If all three connectors 124 are connected to corresponding connectors 126, the blanket 100' will form a relatively wider rectangular pad. Alternatively, the flaps 52' and 66' may be slid laterally relative to each other before connecting connectors 124, 126 to create different configurations for the blanket 100'.

In one use, the patient is laid upon a table with arms outstretched at an angle of 90 degrees relative to the patient's body or at the patient's side at an angle of 0 degrees or at an angle between 0 and 90 degrees. The patient may also be positioned with one or both arms outstretched above shoulder level at an angle greater than 90 degrees. The arm may be supported by a lateral table portion or arm portion of the table. Blanket 100, 100', 200 is placed over the patient's arms and shoulders, with the bridge portion 110, 110', 210 placed behind the patient's head or in the other positions noted above. In this way, the patient's arms are covered by the blanket 100, 100', 200, but some or all of the patient's chest is exposed in area 25, allowing access to the chest area. When the arms are extended at 90 degrees relative to the body, the blanket 100, 100', 200 may be laid flat over the arms. However, if the arms are at an angle other than 90 degrees, the arms portions of the blanket 100, 100', 200 can be adjusted such the arm portions fold or bend to cover the arm. That is, the bridge portion 110, 110', 210 provides sufficient flexibility to the blanket 100, 100', 200 to allow one or both arm portions to be freely manipulated, including tucked at the patient's side or across the patient's body. Blanket 100 may be secured around the patient's arms with strap 70, 80, which may extend around the arm or around the bottom surface of the lateral table portion beneath the arm. The distal ends 74, 84 of strap 70, 80 can be secured to anchor points 170, 180 with one of notches 76, 86. This can create an enclosed space about the patient's arms between the blanket and the lateral table portions to further prevent heat from escaping. In an alternative embodiment, proximal ends 72, 82 of straps 70, 80 may be mounted to rear surface of blanket 100. As noted above, blanket 200 may be secured to the patient via a disposable cover or other secondary mechanism. Also as noted above, blanket 100' may be secured to the patient via the use of slots 122 and a strap.

In other uses, blankets 100, 100', or 200 may be placed over other body parts of the patient, including the patient's legs, one of the patients arms, the patient's hip, etc. The connection mechanisms described above are adaptable enough to secure the blanket 100, 100', and 200 against the patient in many different configurations.

Figure 3A:
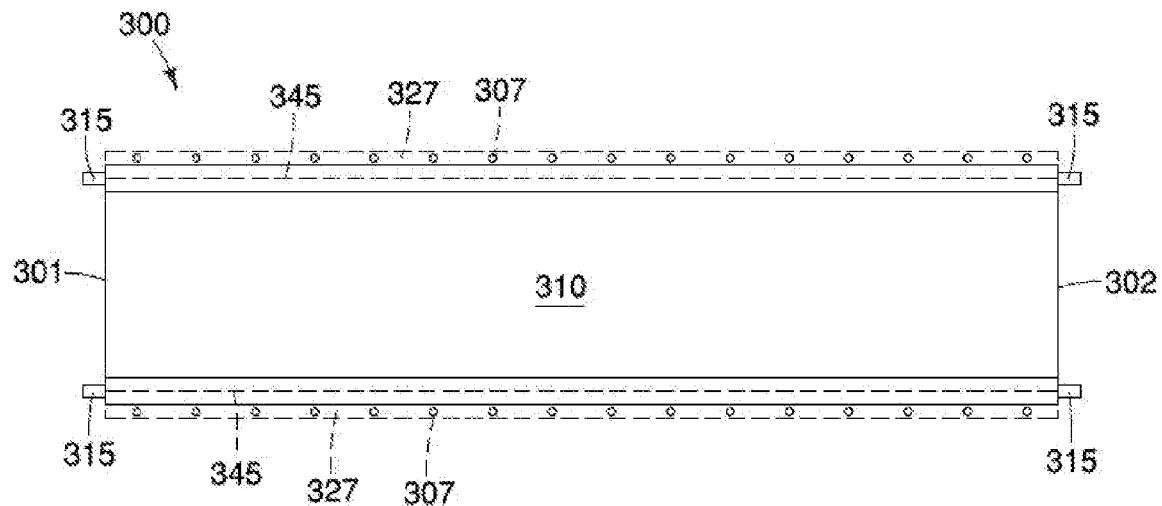
FIG. 3A is a plan view of a flexible heating blanket subassembly for a heating blanket, according to some embodiments of the present invention.
Figure 3B:
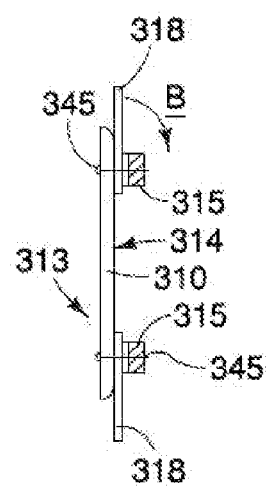
FIG. 3B is an end view of some embodiments of the subassembly shown in FIG. 3A.

FIG. 3A is a plan view of a flexible heating blanket subassembly 300, according to some embodiments of the present invention; and FIG. 3B is an end view of an embodiment of the subassembly shown in FIG. 3A. FIG. 3A illustrates a flexible sheet-like heating element 310, or heater, of subassembly 300 including a first end 301 and a second end 302. According to preferred embodiments of the present invention, heating element 310 comprises a conductive fabric or a fabric incorporating closely spaced conductive elements such that heating element 310 has a substantially uniform watt density output, preferably less than approximately 0.5 watts/sq. inch, and more preferably between approximately 0.2 and approximately 0.4 watts/sq. inch, across a surface area, of one or both sides 313, 314 (FIG. 3B). In some embodiments, the substantially uniform watt density output results from the generally uniform resistance per unit area that remains generally constant, independent of temperature.

Some examples of conductive fabrics which may be employed by embodiments of the present invention include, without limitation, carbon fiber fabrics, fabrics made from carbonized fibers, conductive films, or woven or non-woven non-conductive fabric or film substrates coated with a conductive material, for example, polypyrrole, carbonized ink, or metalized ink. In many embodiments, the conductive fabric is a polymeric fabric coated with a conductive polymeric material such as polypyrrole. In addition, the flexible heating element may be made from a matrix of electrically resistant wire or metal traces attached to a fibrous or film material layer.

FIG. 3A further illustrates subassembly 300 including two bus bars 315 coupled to heating element 310 for powering heating element 310; each bar 315 is shown extending between first and second ends 301, 302. With reference to FIG. 3B, according to some embodiments, bus bars 315 are coupled to heating element 310 by a stitched coupling 345, for example, formed with conductive thread such as silver-coated polyester or nylon thread (Marktek Inc., Chesterfield, Mo.). FIG. 3B illustrates subassembly 300 wherein insulating members 318, for example, fiberglass material strips having an optional PTFE coating and a thickness of approximately 0.003 inch, extend between bus bars 315 and heating element 310 at each stitched coupling 345, so that electrical contact points between bars 315 and heating element 310 are solely defined by the conductive thread of stitched couplings 345. Alternatively, the electrical insulation material layer could be made of polymeric film, a polymeric film reinforced with a fibrous material, a cellulose material, a glass fibrous material, rubber sheeting, polymeric or rubber coated fabric or woven materials or any other suitable electrically insulating material. Each of the conductive thread stitches of coupling 345 maintains a stable and constant contact with bus bar 315 on one side and heating element 310 on the other side of insulating member 318. Specifically, the stitches produce a stable contact in the face of any degree of flexion, so that the potential problem of intermittent contact between bus bar 315 and heating element 310 can be avoided. The stitches are the only electrical connection between bus bar 315 and heating element 310, but, since the conductive thread has a much lower electrical resistance than the conductive fabric of heating element 310, the thread does not heat under normal conditions. In addition to heating blanket applications described herein, such a design for providing for a uniform and stable conductive interface between a bus bar and a conductive fabric heater material can be used to improve the conductive interface between a bus bar or electrode and a conductive fabric in non-flexible heaters, in electronic shielding, in radar shielding and other applications of conductive fabrics.

Preferably, coupling 345 includes two or more rows of stitches for added security and stability. However, due to the flexible nature of blanket subassembly 300, the thread of stitched couplings 345 may undergo stresses that, over time and with multiple uses of a blanket containing subassembly 300, could lead to one or more fractures along the length of stitched coupling 345. Such a fracture, in other designs, could also result in intermittent contact points, between bus bar 315 and heating element 310, that could lead to a melt down of heating element 310 along bus bar. But, if such a fracture were to occur in the embodiment of FIG. 3B, insulating member 318 may prevent a meltdown of heating element 310, so that only the conductive thread of stitched coupling 345 melts down along bus bar 315.

Alternative threads or yarns employed by embodiments of the present invention may be made of other polymeric or natural fibers coated with other electrically conductive materials; in addition, nickel, gold, platinum and various conductive polymers can be used to make conductive threads. Metal threads such as stainless steel, copper or nickel could also be used for this application. According to an exemplary embodiment, bars 315 are comprised of flattened tubes of braided wires, such as are known to those skilled in the art, for example, a flat braided silver coated copper wire, and may thus accommodate the thread extending therethrough, passing through openings between the braided wires thereof. In addition such bars are flexible to enhance the flexibility of blanket subassembly 300. According to alternate embodiments, bus bars 315 can be a conductive foil or wire, flattened braided wires not formed in tubes, an embroidery of conductive thread, or a printing of conductive ink. Preferably, bus bars 315 are each a flat braided silver-coated copper wire material, since a silver coating has shown superior durability with repeated flexion, as compared to tin-coated wire, for example, and may be less susceptible to oxidative interaction with a polypyrrole coating of heating element 310 according to an embodiment described below. Additionally, an oxidative potential, related to dissimilar metals in contact with one another is reduced if a silver-coated thread is used for stitched coupling 345 of a silver-coated bus bar 315.

According to some preferred embodiments, two or more rows of stitches are applied to each bus bar 315 for added safety and stability of the bus bar/heating element interface. The shape of a surface area of heating element 310 is suited for use as a heating assembly 150, 160 of a multi-zone heating blanket, for example, blankets 100, 100', 200 shown in FIGS. 1A, 1B, and 2, that would, for instance, cover an outstretched arm and shoulder of a patient. Of course, the shape of heating element 310 may also be appropriate to cover the leg or side of a patient.

According to an exemplary embodiment, a conductive fabric comprising heating element 310 comprises a non-woven polyester having a basis weight of approximately 170 g/m$^2$ and being 100% coated with polypyrrole (available from Eeonyx Inc., Pinole, Calif.); the coated fabric has an average resistance, for example, determined with a four point probe measurement, of approximately 15 ohms per square inch, which is suitable to produce the preferred watt density of 0.2 to 0.4 watts/sq. in. for surface areas of heating element 310 having a width, between bus bars 315, in the neighborhood of about 10 to 15 inches, when powered at about 48 volts. In some embodiments, the basis weight of the non-woven polyester may be chosen in the range of approximately 80-180 g/m$^2$. However, other basis weights may be engineered to operate adequately and are therefore within the scope of embodiments of the invention.

According to an exemplary embodiment for an adult multi-zone heating blanket, a distance between a first end 301 of heating element 310 and a second end 302 of heating element 310 is between about 30 and 40 inches, while a distance between the bus bars 15 is about 10 to 15 inches. Such a width is suitable for a multi-zone heating blanket, some embodiments of which will be described below. A resistance of such a conductive fabric may be tailored for different widths between bus bars (wider requiring a lower resistance and narrower requiring a higher resistance) by increasing or decreasing a surface area of the fabric that can receive the conductive coating, for example by increasing or decreasing the basis weight of the non-woven. In addition, the resistance employed will vary depending on how the multiple heating assemblies 150 are wired together. Heating assemblies 150 wired together in series will require less resistive configurations than those wired in parallel. The wiring of multiple heating assemblies 150 is discussed further below. Resistance over the surface area of the conductive fabrics is generally uniform in many embodiments of the present invention. However, the resistance over different portions of the surface area of conductive fabrics such as these may vary, for example, due to variation in a thickness of a conductive coating, variation within the conductive coating itself, variation in effective surface area of the substrate which is available to receive the conductive coating, or variation in the density of the substrate itself. Local surface resistance across a heating element, for example heating element 310, is directly related to heat generation according to the following relationship:

$$Q(\text{Joules}) = I^2(\text{Amps}) \times R(\text{Ohms})$$

Variability in resistance thus translates into variability in heat generation, which manifests as a variation in temperature. According to preferred embodiments of the present invention, which are employed to warm patients undergoing surgery, precise temperature control is desirable. Means for determining heating element temperatures, which average out temperature variability caused by resistance variability across a surface of the heating element, are described below in conjunction with FIG. 4A.

A flexibility of blanket subassembly 300, provided primarily by flexible heating element 310, and optionally enhanced by the incorporation of flexible bus bars, allows blanket subassembly 300 to conform to the contours of a body, for example, all or a portion of a patient undergoing surgery, rather than simply bridging across high spots of the body; such conformance may optimize a conductive heat transfer from heating element 310 to a surface of the body.

The uniform watt-density output across the surface areas of preferred embodiments of heating element 310 translates into generally uniform heating of the surface areas, but not necessarily a uniform temperature. At locations of heating element 310 which are in conductive contact with a body acting as a heat sink, for example the heat is efficiently drawn away from heating element 310 and into the body, for example by blood flow, while at those locations where heating element 310 does not come into conductive contact with the body, an insulating air gap exists between the body and those portions, so that the heat is not drawn off those portions as easily. Therefore, those portions of heating element 310 not in conductive contact with the body will gain in temperature, since heat is not transferred as efficiently from these portions as from those in conductive contact with the body. The 'non-contacting' portions will reach a higher equilibrium temperature than that of the 'contacting' portions, when the radiant and convective heat loss equal the constant heat production through heating element 310. Since the heat generation is generally uniform, the heat flux to the patient will also be generally uniform. However, at the non-contacting locations, the temperature is higher to achieve the same flux as the contacting portions. Some of the extra heat from the higher temperatures at the non-contacting portions is therefore dissipated out the back of the pad instead of into the patient. Although radiant and convective heat transfer are more efficient at higher heater temperatures, the laws of thermodynamics dictate that as long as there is a uniform watt-density of heat production, even at the higher temperature, the radiant and convective heat transfer from a blanket of this construction will result in a generally uniform heat flux from the blanket. Therefore, by controlling the 'contacting' portions to a safe temperature, for example, via a temperature sensor assembly 321 coupled to heating element 310 in a location where heating element 310 will be in conductive contact with the body as shown in FIG. 4A, the 'non-contacting' portions, will also be operating at a safe temperature because of the less efficient radiant and convective heat transfer. According to preferred embodiments, heating element 310 comprises a conductive fabric having a relatively small thermal mass so that when a portion of the heating element that is operating at the higher temperature is touched, suddenly converting a 'non-contacting' portion into a 'contacting' portion, that portion will cool almost instantly to the lower operating temperature. According to the embodiment illustrated in FIG. 4A, temperature sensor assembly 321 is coupled to heating element 310 at a location where heating element 310, when incorporated in a multi-zone heating blanket, for example, blanket 100, would come into heat conductive contact with the patient in order to maintain a safe temperature distribution across heating element 310.

With reference to FIG. 4A, in conjunction with FIG. 2, it may be appreciated that temperature sensor assembly 321 is located on assembly 350 so that, when blanket 200 including assembly 350 is draped over the upper body of the patient, the area of heating element 310 surrounding sensor assembly 321 will be in conductive contact with the shoulder area of the patient in order to maintain a safe temperature distribution across heating element 310.

Embodiments of the invention include two separate zones of heating element 310, with one in each body part portion. Embodiments of the invention may therefore include a temperature sensor assembly 321 in either one of the zones or in both zones. In embodiments in which include only one sensor, the heating element 310 without the sensor is slaved off of the control of the heating element with the sensor. Proper operation of the heating elements 310 is ensured by matching the Watt densities of the two heating elements 310. If two temperature sensor assemblies 321 are used with one in each zone of the heating elements 310, the two temperature sensor assemblies 321 can be connected to a multi-zone temperature controller that can separately control each zone. Alternately, the two sensors can be connected to a multiplexer that shifts the temperature sensing input back and forth between the two zones. The multiplexer transmits the temperature of each zone to a single zone temperature controller. The control of the heating elements 310 can be based on the temperatures of the zones, such as the highest, the lowest or the average temperature of the two zones.

According to embodiments of the present invention, sections of heating element 310 may be differentiated according to whether or not portions of heating element 310 are in conductive contact with a body, for example, a patient undergoing surgery. In the case of conductive heating, gentle external pressure may be applied to a heating blanket including heating element 310, which pressure forces heating element 310 into better conductive contact with the patient to improve heat transfer. However, if excessive pressure is applied the blood flow to that skin may be reduced at the same time that the heat transfer is improved and this combination of heat and pressure to the skin can be dangerous. It is well known that patients with poor perfusion should not have prolonged contact with conductive heat in excess of approximately 42° C. 42° C. has been shown in several studies to be the highest skin temperature, which cannot cause thermal damage to normally perfused skin, even with prolonged exposure. (Stoll & Greene, Relationship between pain and tissue damage due to thermal radiation. J. Applied Physiology 14(3):373-382. 1959. and Moritz and Henriques, Studies of thermal injury: The relative importance of time and surface temperature in the causation of cutaneous burns. Am. J. Pathology 23:695-720, 1947). Thus, according to certain embodiments of the present invention, the portion of heating element 310 that is in conductive contact with the patient is controlled to approximately 43° C. in order to achieve a temperature of about 41-42° C. on a surface a heating blanket cover that surrounds heating element 310, for example, a cover or shell portion 50, 60 which was described above in conjunction with FIG. 1A.

FIG. 4A is a top plan view of a heating element assembly 350, according to some embodiments of the present invention, which may be incorporated as assembly 150 or 160 in blanket 100, 100', 200, which is shown, for example, in FIGS. 1A, 1B, and 2. FIGS. 4A and 4B illustrate a temperature sensor assembly 321 assembled on side 314 of heating element and heating element 310 overlaid on both sides 313, 314 with an electrically insulating layer 330, preferably formed of a flexible non-woven, or non-woven fibrous material, for example, 1.5 OSY (ounces per square yard) nylon, which is preferably laminated to sides 313, 314 with a hotmelt laminating adhesive. In some embodiments, the adhesive is applied over the entire interfaces between insulating layer 330 and heating element 310. Other examples of suitable materials for insulating layer 330 include, without limitation, polymeric foam, a woven fabric, such as cotton or fiberglass, and a relatively thin plastic film, cotton, and a non-flammable material, such as fiberglass or treated cotton. According to preferred embodiments, overlaid insulating layers 330, without compromising the flexibility of heating assembly 350, prevent electrical shorting of one portion of heating element 310 with another portion of heating element 310 if heating element 310 is folded over onto itself. Heating element assembly 350 may be enclosed within a relatively durable and waterproof shell, for example shell portion 50 shown with dashed lines in FIG. 4B, and will be powered by a relatively low voltage (approximately 48V). Insulating layers 330 may even be porous in nature to further maintain the desired flexibility of assembly 350.

FIG. 4A further illustrates junctions 355 coupling leads 305 to each bus bar 315, and another lead 306 coupled to and extending from temperature sensor assembly 321; each of leads 305, 306 extend over insulating layer 330 and into an electrical connector housing 325 (also shown in FIG. 1) containing a connector plug 323, which will be described in greater detail below, in conjunction with FIG. 5A. Returning now to FIG. 4B, temperature sensor assembly 321 will be described in greater detail. FIG. 4B illustrates sensor assembly 321 including a substrate 331, for example, of polyimide (Kapton), on which a temperature sensor 351, for example, a surface mount chip thermistor (such as a Panasonic ERT-J1VG103FA: 10K, 1% chip thermistor), is mounted; a heat spreader 332, for example, a copper or aluminum foil, is mounted to an opposite side of substrate 331, for example, being bonded with a pressure sensitive adhesive; substrate 331 is relatively thin, for example about 0.0005 inch thick, so that heat transfer between heat spreader 332 and sensor 351 is not significantly impeded.

Sensor 351, according to embodiments of the present invention, is positioned such that, when a heating blanket including heating element 310 is placed over a body, the regions surrounding sensor 351 will be in conductive contact with the body. As previously described, it is desirable that a temperature of approximately 43° C. be maintained over a surface of heating element 310 which is in conductive contact with a body of a patient undergoing surgery. An additional alternate embodiment is contemplated in which an array of temperature sensors are positioned over the surface of heating element 310, being spaced apart so as to collect temperature readings which may be averaged to account for resistance variance.

Figure 5A:
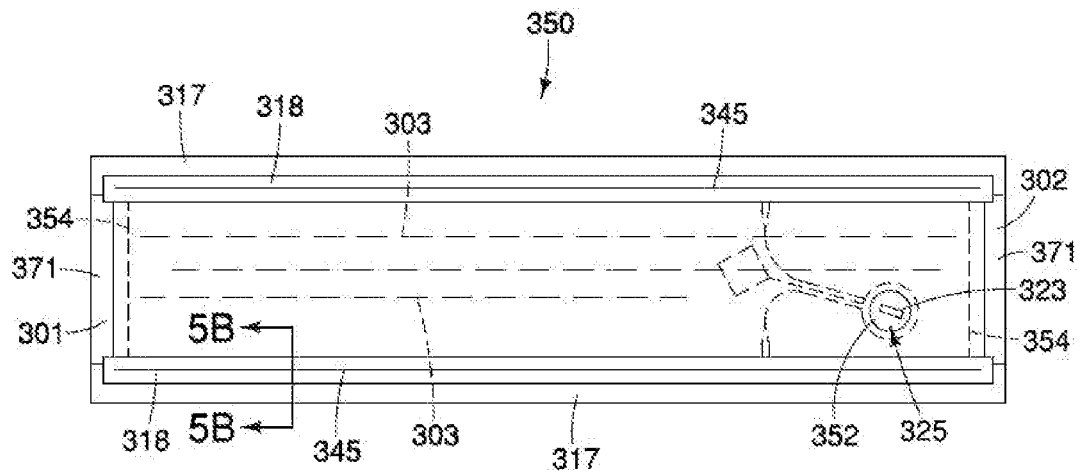
FIG. 5A is a top plan view of a heating element assembly, which may be incorporated in the blanket shown in FIG. 1A or 1B.
Figure 5B:
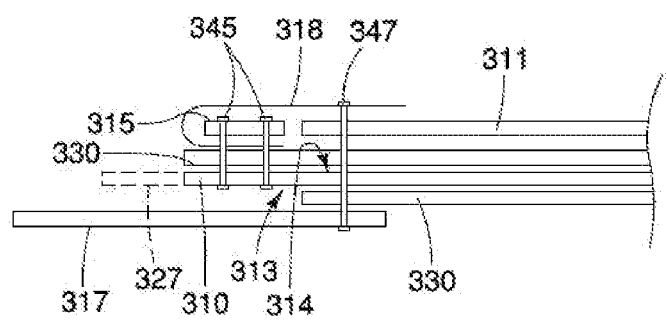
FIG. 5B is a cross-section view through section line 5B-5B of FIG. 5A.

FIG. 5A is a top plan view of heating element assembly 350, which may be incorporated into heating assembly 150, 160 of blankets 100, 100', 200; and FIG. 5B is a cross-section view through section line 5B-5B of FIG. 5A. FIGS. 5A-B illustrate heating element assembly 350 including heating element 310 overlaid with electrical insulation 330 on both sides 313, 314 and thermal insulation layer 311 extending over the top side 314 thereof (dashed lines show leads and sensor assembly beneath layer 311).

Blankets 100, 100', 200 may include a layer of thermal insulation 311 extending over a top side (corresponding to side 314 of heating element 310 as shown in FIG. 3B) of heating assemblies 150, 160. The layer of thermal insulation may or may not be bonded to a surface of assemblies 150, 160. It may serve to prevent heat loss away from a body disposed on the opposite side of blanket 100, 100', 200, particularly if a heat sink comes into contact with the top side of blanket 100, 100', 200. The insulation layer may extend over an entire surface of side 314 (FIG. 3B) of heating element 310 (top surface) and over sensor assembly 321 (FIGS. 4A-4B)

and may be secured to heating element assemblies 150, 160 as will be described in greater detail below. In different embodiments, layer 311 comprises any, or a combination of the following: a non-woven material (e.g., a CDS200 Thinsulate by 3M), other high loft fibrous polymeric non-woven materials, non-woven cellulose material, and air, for example, held within a polymeric film bubble. In some embodiments, the insulating layer comprises a polymer foam, for example, a 2 pound density 50 ILD urethane foam, which has a thickness between approximately ⅛$^{th}$ inch and approximately ¾$^{th}$ inch.

According to the illustrated embodiment, layer 311 is inserted beneath a portion of each insulating member 318, each which has been folded over the respective bus bar 315, for example as illustrated by arrow B in FIG. 3B, and then held in place by a respective row of non-conductive stitching 347 that extends through insulating member 318, layer 311 and heating element 310. Although not shown, it should be appreciated that layer 311 may further extend over bus bars 315. Although insulating layer 330 is shown extending beneath layer 311 on side 314 of heating element, according to alternate embodiments, layer 311 independently performs as a thermal and electrical insulation so that insulating layer 330 is not required on side 314 of heating element 310. FIG. 5A further illustrates, with longitudinally extending dashed lines, a plurality of optional slits 303 in layer 311, which may extend partially or completely through layer 311, in order to increase the flexibility of assembly 350. Such slits are desirable if a thickness of layer 311 is such that it prevents blanket 100, 100', 200 from draping effectively about a patient; the optional slits are preferably formed, for example, extending only partially through layer 311 starting from an upper surface thereof, to allow bending of blanket 100, 100', 200 about a patient and to prevent bending of blanket 100, 100', 200 in the opposition direction.

Returning now to FIG. 4A, to be referenced in conjunction with FIG. 5A, connector housing 325 and connector plug 323 will be described in greater detail. According to certain embodiments, housing 325 is an injection molded thermoplastic, for example, PVC, and may be coupled to assembly 350 by being stitched into place, over insulating layer 330. FIG. 4A shows housing 325 including a flange 353 through which such stitching can extend. Connector plug 323 protrudes from shell portion 50 of blanket 100 so that an extension cable may couple bus bars to a power source, and temperature sensor assembly 321 to a temperature controller, both of which may be incorporated into a console. In certain embodiments, the power source supplies a pulse-width-modulated voltage to bus bars 315. The controller may function to interrupt such power supply (e.g., in an over-temperature condition) or to modify the duty cycle to control the heating element temperature. In some embodiments, a surface of flange of housing 325 (FIG. 5A) protrudes through a hole formed in thermal insulating layer 311 so that a seal may be formed, for example, by adhesive bonding and/or heat sealing, between an inner surface of shell portions 50, 60 and surface 352. According to one embodiment, wherein housing 325 is injection molded PVC and the inner surface of shell portions 50, 60 is coated with polyurethane, housing 325 is sealed to shell portion 50 via a solvent bond. It may be appreciated that the location of the connector plug 323 is suitable to keep the corresponding connector cord well away from the surgical field.

FIGS. 5A-B further illustrate a pair of securing strips 317, each extending laterally from and alongside respective lateral portions of heating element 310, parallel to bus bars 315, and each coupled to side 313 of heating element 310 by the respective row of non-conductive stitching 347. Another pair of securing strips 371 is shown in FIG. 5A, each strip 371 extending longitudinally from and alongside respective ends 301, 302 of heating element 310 and being coupled thereto by a respective row of non-conductive stitching 354. Strips 371 may extend over layer 311 or beneath heating element 310. Strips 317 preferably extend over conductive stitching of stitched coupling 345 on side 313 of heating element 310, as shown, to provide a layer of insulation that can prevent shorting between portions of side 313 of heating element 310 if heating element 310 were to fold over on itself along rows of conductive stitching of stitched coupling 345 that couple bus bars 315 to heating element 310; however, strips 317 may alternately extend over insulating member 318 on the opposite side of heating element 310. According to the illustrated embodiment, securing strips 317 and 371 are made of a polymer material, for example, PVC. They may be heat sealed between the sheets of shell portions 50, 60 in corresponding areas of the heat seal zone in order to secure heating element assembly 350 within a corresponding gap between the two sheets of shell portions 50, 60. According to an alternate embodiment, for example, shown by dashed lines in FIGS. 3A and 5B, heating element 310 extends laterally out from each bus bar 315 to a securing edge 327, which may include one or more slots or holes 307 extending therethrough so that inner surfaces of sheets of shell portions 50, 60 can contact one another to be sealed together and thereby hold edges 327.

Figure 6:
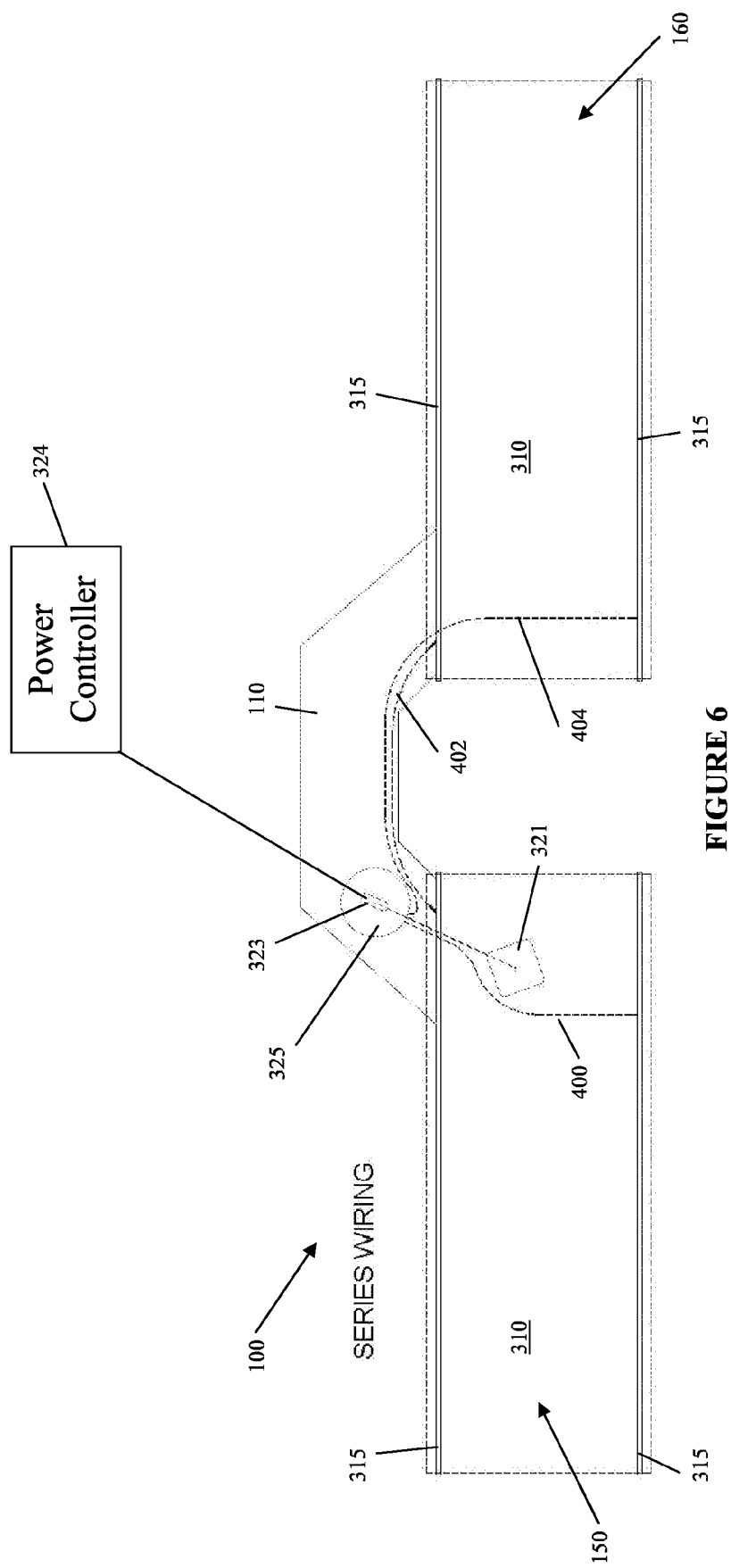
FIG. 6 is a schematic view of a multi-zone heating blanket, according to some embodiments of the present invention, showing series wiring.

The first and second heating assemblies can be wired in series or in parallel. An embodiment of the blanket 100 (or 100' or 200) in which the heating assemblies 150, 160 are wired in series is shown in FIG. 6. Wiring the heating assemblies 150, 160 in series can provide for increased safety because the failure of one heating assembly causes both to fail. For instance, as shown in FIG. 6, the power supplied by the power controller 324 connects to housing 325 via a connector plug 323. The current passes from connector plug 323 to a first bus bar 315 of assembly 150 via wire 400, where it flows to the second bus bar 315 of assembly 150 via heating element 310. The current then flows to a first bus bar 315 of assembly 160 via wire 402 that passes through the bridge portion 110, where it flows to the second bus bar 315 of the assembly 160 via heating element 310. The current then returns back to the connector plug 323 via wire 404 that again passes through the bridge portion 110. In this manner, a failure of any of the components will interrupt current flow for the entire blanket. Although one temperature sensor assembly 321 is shown, multiple temperature sensors may be included as described above.

FIG. 7 depicts an embodiment of the blanket 100 (or 100' or 200) in which the heating assemblies 150, 160 are wired in parallel. In this embodiment, power supplied by the power controller connects to housing 325 via connector plug 323. The power from connector plug 323 is connected to a first bus bar 315 of assembly 150, where it flows to the second bus bar 315 of assembly 150 via heating element 310. The power then returns back to the connector via wire 412. Assembly 160 is powered in parallel with assembly 150 via the use of interconnecting wires 414 and 416 that connect the bus bars 315 together and pass through bridge portion 110. Wire 414 connects bus bar 315 of assembly 150 with bus bar 315 of assembly 160 to transfer the supply voltage from connector plug 323 to bus bar 315. Wire 416 connects bus bar 315 of assembly 150 to bus bar 315 of assembly 160 to transfer the return line to connector plug 323 to bus bar 315 of assembly 160. In this embodiment, the zones have balanced resistances to assure even heating.

In the foregoing detailed description, the invention has been described with reference to specific embodiments. However, it may be appreciated that various modifications and changes can be made without departing from the scope of the invention as set forth. Although embodiments of the invention are described in the context of a hospital operating room, it is contemplated that some embodiments of the invention may be used in other environments. Those embodiments of the present invention, which are not intended for use in an operating environment and need not meet stringent FDA requirements for repeated used in an operating environment, need not include particular features described herein, for example, related to precise temperature control. Thus, some of the features of preferred embodiments described herein are not necessarily included in preferred embodiments of the invention which are intended for alternative uses.

The invention claimed is:

1. A multi-zone electric heating blanket, comprising:
an elongate first body part portion having proximal and distal ends, the first body part portion including a first heating element assembly and adapted for placement over a first body part of a patient;
an elongate second body part portion having proximal and distal ends, the second body part portion including a second heating element assembly and adapted for placement over a second body part of the patient;
a bridge portion interconnecting the first body part portion and the second body part portion at or near the proximal ends thereof; and
a temperature sensor coupled to the first heating element assembly and configured to measure a temperature of the first heating element assembly, wherein the temperature sensor controls the temperature of both the first heating element assembly and the second heating element assembly.

2. The heating blanket of claim 1, wherein the bridge portion is unheated.

3. The heating blanket of claim 1, wherein the bridge portion is flexible.

4. The heating blanket of claim 1, wherein the bridge portion electrically connects the first heating element assembly to the second heating element assembly.

5. The heating blanket of claim 1, wherein the bridge portion consists essentially of an electrical cable.

6. The heating blanket of claim 1, wherein the first heating element assembly is about 10 to 15 inches wide.

7. The heating blanket of claim 1, further including straps adapted for securing the heating blanket against the patient.

8. The heating blanket of claim 1, wherein the first and second body parts are first and second arms of the patient.

9. The heating blanket of claim 8, wherein the bridge portion is adapted for placement under the head of the patient, whereby the weight of the patient's head will stabilize the position of the heating blanket.

10. A multi-zone electric heating blanket, comprising:
an elongate first body part portion having proximal and distal ends, the first body part portion including a first electrical heating element and adapted for placement over a first body part of the patient;
an elongate second body part portion having proximal and distal ends, the second body part portion including a second electrical heating element and adapted for placement over a second body part of the patient;
a bridge portion electrically interconnecting the first electrical heating element and the second heating element;
a temperature sensor coupled to the first heating element and configured to measure a temperature of the first heating element; and
a power controller supplying power to the first heating element and the second heating element, wherein power flows through at least a portion of the first heating element before flowing to the second heating element.

11. The heating blanket of claim 10, wherein the first body part portion includes one or more unheated flaps extending from one or more locations around the perimeter of the first heating element assembly.

12. The heating blanket of claim 11, wherein the one or more unheated flaps may be tucked under the first body part of the patient.

13. The heating blanket of claim 11, wherein the one or more unheated flaps contain weights causing the flaps to hang down along the first body part of the patient when the first body part portion is placed over the first body part of the patient.

14. The heating blanket of claim 11, wherein the unheated flaps contain one or more slots for receiving a connecting strap, the connecting strap adapted for securing the heating blanket against the patient.

15. The heating blanket of claim 11, wherein the second body part portion includes one or more unheated flaps extending from one or more locations around the perimeter of the second heating element assembly.

16. The heating blanket of claim 11, wherein the unheated flaps of the first body part portion and the second body part portion contain one or more connectors, the unheated flaps of the first body part portion being connectable to the unheated flaps of the second body part portion via the one or more connectors, whereby a wide blanket may be formed by such a connection.

17. The heating blanket of claim 10, wherein the bridge portion comprises electrical wiring.

18. The heating blanket of claim 17, wherein the bridge portion consists essentially of electrical wiring.

19. The heating blanket of claim 10, wherein the first heating element assembly and the second heating element assembly are wired in series with the power supply, whereby an open circuit failure of one of the first and second heating element assemblies interrupts current flow to the other one of the first and second heating element assemblies.

20. The heating blanket of claim 10, wherein the blanket is wired such that power is supplied in parallel to the first heating element assembly and the second heating element assembly.

21. A multi-zone electric heating blanket, comprising:
an elongate first body part portion having proximal and distal ends, the first body part portion including a first heating element assembly and adapted for placement over a first body part of the patient, the first heating element assembly including two conductive bus bars electrically connected via a first conductive sheet;
an elongate second body part portion having proximal and distal ends, the second body part portion including a second heating element assembly and adapted for placement over a second body part of the patient, the second heating element assembly including two conductive bus bars electrically connected via a second conductive sheet, the first conductive sheet and the second conductive sheet producing approximately equal watt density outputs when powered;
a bridge electrically interconnecting the bus bars of the first heating element assembly and the second heating element assembly;

a temperature sensor coupled to only one of the first conductive sheet and the second conductive sheet and configured to measure a temperature of the first conductive sheet; and a power controller operatively connected to the electric heating blanket for supplying power to the first heating element assembly and the second heating element assembly, the power supplied to both the first heating element assembly and the second heating element being based on the temperature sensed by the temperature sensor;

wherein the first heating element assembly and the second heating element assembly are wired in series with the power supply, whereby an open circuit failure of one of the first and second heating element assemblies interrupts current flow to the other one of the first and second heating element assemblies.

22. A method of using an upper body electric heating blanket shaped to cover the outstretched arms and shoulders of a patient while leaving the chest exposed, comprising:

placing the upper body electric heating blanket over the arms and shoulders of the patient, the blanket having a first and second flexible sheet-like heating element and a first and second flexible shell covering the heating elements, a proximal end of the first shell connected to a proximal end of the second shell by a bridge portion, and;

positioning the blanket such that the bridge portion is located beneath the patient's head such that the patient's head stabilizes the bridge portion and the first and second heating elements in a position.

23. A multi-zone electric heating blanket, comprising:

an elongate first body part portion having proximal and distal ends, the first body part portion including a first heating element assembly and adapted for placement over a first body part of the patient, the first heating element assembly including two conductive bus bars electrically connected via a first conductive sheet;

an elongate second body part portion having proximal and distal ends, the second body part portion including a second heating element assembly and adapted for placement over a second body part of the patient, the second heating element assembly including two conductive bus bars electrically connected via a second conductive sheet, the first conductive sheet and the second conductive sheet producing approximately equal watt density outputs when powered;

a bridge electrically interconnecting the bus bars of the first heating element assembly and the second heating element assembly;

a temperature sensor coupled to only one of the first conductive sheet and the second conductive sheet and configured to measure a temperature of the first conductive sheet; and a power controller operatively connected to the electric heating blanket for supplying power to the first heating element assembly and the second heating element assembly, the power supplied to both the first heating element assembly and the second heating element being based on the temperature sensed by the temperature sensor;

wherein the blanket is wired such that power is supplied in parallel to the first heating element assembly and the second heating element assembly; and wherein the first and second heating element assemblies have balanced electrical resistance.

* * * * *

UNITED STATES PATENT AND TRADEMARK OFFICE
CERTIFICATE OF CORRECTION

PATENT NO. : 8,986,359 B2
APPLICATION NO. : 12/249896
DATED : March 24, 2015
INVENTOR(S) : Scott D. Augustine et al.

Page 1 of 1

It is certified that error appears in the above-identified patent and that said Letters Patent is hereby corrected as shown below:

Title page

Item (75) Inventors: "Scott D. Augustine, Bloomington, MN (US); Ryan S. Augustine, Minneapolis, MN (US); Randall C. Arnold, Minnetonka, MN (US); Keith J. Leland, Medina, MN (US); Joshua P. Waldman, Edina, MN (US); Rudolf A. Deibel, Eden Prairie, MN (US); Thomas F. Neils, Minneapolis, MN (US)" should read --"Scott D. Augustine, Bloomington, MN (US); Ryan S. Augustine, Minneapolis, MN (US); Randall C. Arnold, Minnetonka, MN (US); Keith J. Leland, Medina, MN (US); Rudolf A. Deibel, Eden Prairie, MN (US); Thomas F. Neils, Minneapolis, MN (US)"--

Signed and Sealed this
First Day of March, 2016

Michelle K. Lee
*Director of the United States Patent and Trademark Office*